US008158192B2

(12) United States Patent
Bothe et al.

(10) Patent No.: US 8,158,192 B2
(45) Date of Patent: Apr. 17, 2012

(54) PROCESS FOR THE COATING OF BIOMEDICAL ARTICLES

(75) Inventors: Harald Bothe, Wiesbaden (DE); Yasuo Matsuzawa, Roswell, GA (US); Bernhard Seiferling, Goldbach (DE); Katharina Schmid, Aschaffenburg (DE); Heike Arndt, Mömlingen (DE)

(73) Assignee: Novartis AG, Basel (CH)

( * ) Notice: Subject to any disclaimer, the term of this patent is extended or adjusted under 35 U.S.C. 154(b) by 1106 days.

(21) Appl. No.: 12/004,002

(22) Filed: Dec. 19, 2007

(65) Prior Publication Data
US 2008/0152800 A1 Jun. 26, 2008

(30) Foreign Application Priority Data

Dec. 21, 2006 (EP) ..................................... 06126835

(51) Int. Cl.
*A45C 11/04* (2006.01)
*B65D 85/38* (2006.01)
(52) U.S. Cl. ...................... 427/164; 351/160 H; 206/5.1
(58) Field of Classification Search .................. 427/164; 351/160 H; 206/5.1
See application file for complete search history.

(56) References Cited

U.S. PATENT DOCUMENTS

| | | | |
|---|---|---|---|
| 4,168,112 A | 9/1979 | Ellis | |
| 4,321,261 A | 3/1982 | Ellis | |
| 4,941,997 A | 7/1990 | Decher | |
| 4,973,429 A | 11/1990 | Decher | |
| 5,068,318 A | 11/1991 | Decher | |
| 5,208,111 A | 5/1993 | Decher | |
| 5,336,797 A | 8/1994 | McGee | |
| 5,509,899 A | 4/1996 | Fan | |
| 5,518,767 A | 5/1996 | Rubner | |
| 5,529,727 A | 6/1996 | LaBombard | |
| 5,536,573 A | 7/1996 | Rubner | |
| 5,700,559 A | 12/1997 | Sheu | |
| 5,800,412 A | 9/1998 | Zhang et al. ................. | 604/280 |
| 6,011,082 A | 1/2000 | Wang | |
| 6,286,955 B1 | 9/2001 | Akashi ...................... | 351/160 H |
| 6,428,839 B1 | 8/2002 | Künzler et al. ................ | 427/2.1 |
| 6,451,871 B1 | 9/2002 | Winterton | |
| 6,478,423 B1 * | 11/2002 | Turner et al. .................. | 351/177 |
| 6,531,432 B2 | 3/2003 | Molock | |
| 6,632,905 B2 | 10/2003 | Leboeuf ..................... | 526/303.1 |
| 6,699,435 B2 | 3/2004 | Salpekar | |
| 6,793,973 B2 | 9/2004 | Winterton et al. ......... | 427/393.5 |
| 6,815,074 B2 | 11/2004 | Aguado et al. ................ | 428/447 |
| 2001/0045676 A1 | 11/2001 | Winterton | |
| 2001/0048975 A1 | 12/2001 | Winterton | |
| 2002/0006493 A1 | 1/2002 | Chabrecek | |
| 2002/0086160 A1 | 7/2002 | Qiu | |
| 2002/0182316 A1 | 12/2002 | Gilliard | |
| 2003/0008154 A1 | 1/2003 | Aguado | |
| 2003/0012872 A1 | 1/2003 | Qiu | |
| 2003/0039742 A1 | 2/2003 | Qiu | |
| 2003/0052424 A1 | 3/2003 | Turner | |
| 2003/0117579 A1 | 6/2003 | Morris | |
| 2003/0125498 A1 | 7/2003 | McCabe | |
| 2003/0134132 A1 | 7/2003 | Winterton | |
| 2003/0143335 A1 | 7/2003 | Qiu | |
| 2003/0162862 A1 | 8/2003 | McCabe | |
| 2004/0018295 A1 | 1/2004 | Qiu | |
| 2004/0047979 A1 | 3/2004 | Qiu | |
| 2004/0067365 A1 | 4/2004 | Qiu | |
| 2004/0108607 A1 | 6/2004 | Winterton | |
| 2006/0251694 A1 | 11/2006 | Nielsen et al. ................ | 424/422 |
| 2008/0213460 A1 | 9/2008 | Benter et al. .................. | 427/2.1 |

FOREIGN PATENT DOCUMENTS

| | | |
|---|---|---|
| EP | 0032443 A2 | 7/1981 |
| EP | 0138385 A2 | 4/1985 |
| EP | 0995762 A2 | 4/2000 |
| GB | 2102070 A | 1/1983 |
| JP | 01050014 A | 2/1989 |
| JP | 01158412 A | 6/1989 |
| JP | 5318118 A2 | 12/1993 |
| JP | 07256844 A | 10/1995 |
| JP | 07266443 A | 10/1995 |
| WO | 9500618 A1 | 1/1995 |
| WO | 9502251 A2 | 1/1995 |
| WO | WO 95/06670 | 3/1995 |
| WO | 9520407 A1 | 8/1995 |
| WO | 9618498 A1 | 6/1996 |
| WO | 9631792 A1 | 10/1996 |
| WO | 9637241 A1 | 11/1996 |
| WO | WO 98/58990 * | 12/1998 |
| WO | 9935520 A1 | 7/1999 |
| WO | 0157118 A2 | 8/2001 |
| WO | 0192924 A1 | 12/2001 |
| WO | 0216974 A2 | 2/2002 |
| WO | 02097481 A1 | 12/2002 |
| WO | 03066714 A1 | 8/2003 |

OTHER PUBLICATIONS

PCT International Search Report.
PCT Written Opinion of the International Searching Authority.
Cheung et al, "Molecular-Level Processing of Conjugated Polymers. 3. Layer-by-Layer Manipulation of Polyaniline via Electrostatic Interactions", Macromolecules 1997, vol. 30, No. 9, pp. 2712-2716.
G. Decher et al. "New nanocomposite films for biosensors: layer-by-layer adsorbed films of polyelectrolytes, proteins or DNA", Biosensors & Bioelectronics 9 (1994) pp. 677-684.

(Continued)

Primary Examiner — Robert D. Harlan
(74) Attorney, Agent, or Firm — Sheng-Hsin Hu

(57) ABSTRACT

The invention relates to a process for the manufacture of a hydrophilic coating on a biomedical article, which comprises treating the biomedical article for a time period of $\leq 5$ minutes with a solution of an organic solvent comprising a polyanionic compound with a number average molecular weight $M_n$ of >5000, wherein the solution comprises less than 10% by weight of water, and wherein the solution is devoid of a cationic polymer.

The coated biomedical articles obtainable by the process of the invention have desirable characteristics regarding adherence to the substrate, durability, hydrophilicity, wettability, biocompatibility and permeability and are thus especially useful in the field of ophthalmic devices.

11 Claims, No Drawings

OTHER PUBLICATIONS

Ferreira and Rubner, "Molecular-Level Processing of Conjugated Polymers. 1. Layer-by-Layer Manipulation of Conjugated Polyions", 1995 American Chemical Society, Macromolecules, 1995, vol. 28, No. 21, pp. 7107-7114.

Fou and Rubner, "Molecular-Level Processing of Conjugated Polymers. 2. Layer-by-Layer Manipulation of In-Situ Polymerized p-Type Doped Conducting Polymers", 1995 American Chemical Society, Macromolecules, 1995, vol. 28, No. 21, pp. 7115-7120.

H. Kaczmarek et al., "Study of poly(acrylic acid)-poly(vinylpyrrolidone) complexes and their photostability", 2001 Elsevier Science Ltd., Polymer 42 (2001), pp. 6057-6069.

Onitsuka et al., "Enhancement of light emitting diodes based on self-assembled heterostructures of poly(p-phenylene vinylene)", 1996 American Institute of Physics, J. Appl. Phys. Oct. 1 1996, vol. 80, No. 7, pp. 4067-4071.

G.B.Sukhorukov et al., "Assembly of polyelectrolyte multilayer films by consecutively alternating adsorption of polynucleotides and polycations", 1996 Elsevier Science S.A., Thin solid Films 284-285 (1996), pp. 220-223.

M. Uchida et al., "Blood compatiblity-surface characteristic relationships of a Langmuir-Blodgett film composed of an anionic amphiphile-polycation complex", VSP 1994, New Polymeric Mater (1994), vol. 4, No. 3, pp. 199-211.

T.G.Vargo et al., "Patterned polymer multilayer fabrication by controlled adhesion of polyelectrolytes to plasma-modified fluoropolymer surfaces", Supramolecular Science (1995), vol. 2, Nos. 3-4, pp. 169-174.

Yoo et al., "Investigations of new self-assembled multilayer thin films based on alternately adsorbed layers of polyelectrolytes and functional dye molecules", 1996 Materials Research Society, vol. 413, pp. 395-400.

Yoo et al., "Layer-by-layer modification of surfaces through the use of self-assembled monolayers of polyions", Antec 1995, pp. 2568-2570.

Yoo et al., "New Electro-active self-assembled multilayer thin films based on alternately adsorbed layers of polyelectrolytes and functional dye molecules", 1997 Elsevier Science S.A., Synthetic Metals 85 (1997), pp. 1425-1426.

Cheung et al., "Molecular Self-Assembly of Conducting Polymers: A New Layer-by-Layer Thin Film Deposition Process", pp. 757-758.

* cited by examiner

PROCESS FOR THE COATING OF BIOMEDICAL ARTICLES

This application claims benefit under 35 USC §119 of European patent application No. EP 06126835.5 filed Dec. 21, 2006, the contents of which are incorporated herein by reference.

The present invention relates to a process for the manufacture of coated articles such as biomedical articles, especially contact lenses, which are at least partly coated with a polyanionic polymer.

A variety of different types of processes for preparing coatings on an "inert" hydrophobic article, in particular on an inert biomedical article such as a silicon hydrogel containing contact lens, have been disclosed in the prior art. EP-A 1 153 964 and EP-A-1 287 060 both disclose polyanionic coatings on silicon hydrogel contact lenses, which are prepared by immersing the contact lenses in an aqueous solution of the polyanionic compound. EP-A 1 252 222 discloses in Example 7 a silicon hydrogel lens coated with a polyacrylic acid and a polyallylamine in a molar ratio of 10:1; the coating is obtained by first swelling the contact lens in isopropyl alcohol, removing the lens from the alcoholic solution and dipping it into an aqueous solution comprising the polyanionic and polycationic component.

The above-mentioned coating processes are in general batch processes, which require extensive handling steps and time. The treatment is usually performed at an elevated temperature, and the treatment times are at least several minutes and in general at least an hour and more. In case the treatment times are shortened, unsatisfactory results are obtained due to an insufficient surface coverage with the ionic component(s). Because of this, none of the existing processes is well suited, for example, for the integration into a fully automated high volume contact lens manufacturing process with short cycle times as described, for example, in EP-A-969956 or EP-A-1047542.

Accordingly, there is a need to provide an improved process for the hydrophilic coating of a biomedical article with a polyanionic compound, which is on the one hand easily integrable in a mass manufacturing process and on the other hand provides hydrophilic coatings with an improved durability and wearer comfort.

Surprisingly, it has now been found, that hydrophobic biomedical articles such as silicon-containing contact lenses may be rendered effectively hydrophilic in a very short time by treating the articles in a substantially anhydrous solution of a polyanionic compound.

The present invention therefore in one aspect concerns a process for the hydrophilic coating of a biomedical article, which comprises treating the biomedical article for a time period of $\leq 5$ minutes with a solution of an organic solvent comprising a polyanionic compound with a number average molecular weight $M_n$ of >5000, wherein the solution comprises less than 10% by weight of water.

The biomedical article according to the invention is, for example, an ophthalmic device, preferably a contact lens including both hard and particularly soft contact lenses, an intraocular lens or an artificial cornea, comprising in each case an organic bulk material. Further examples of suitable biomedical articles are wound healing dressings, eye bandages, materials for the sustained release of an active compound such as a drug delivery patch, moldings that can be used in surgery, such as heart valves, vascular grafts, catheters, artificial organs, encapsulated biologic implants, e.g. pancreatic islets, materials for prostheses such as bone substitutes, or moldings for diagnostics, membranes or biomedical instruments or apparatus.

The organic bulk material underlying the biomedical article is preferably a hydrophobic material that is devoid of ionic groups such as cationic or anionic groups or has at least a relatively low concentration of ionic groups. Accordingly, the surface of the preferred bulk materials also has a low concentration of ionic groups or is even devoid of ionic groups such as carboxy, sulfo, amino and the like groups and thus may be substantially free of ionic charges.

Examples of suitable bulk materials are natural or synthetic organic polymers or modified biopolymers which are known in large number. Some examples of polymers are polyaddition and polycondensation polymers (polyurethanes, epoxy resins, polyethers, polyesters, polyamides and polyimides); vinyl polymers (polyacrylates, polymethacrylates, polyacrylamides, polymethacrylamides, polystyrene, polyethylene and halogenated derivatives thereof, polyvinyl acetate and polyacrylonitrile); or elastomers (silicones, polybutadiene and polyisoprene).

A preferred group of materials to be coated are those being conventionally used for the manufacture of biomedical devices, e.g. contact lenses, in particular contact lenses for extended wear, which are not hydrophilic per se. Such materials are known to the skilled artisan and may comprise for example polysiloxanes, perfluoroalkyl polyethers, fluorinated poly(meth)acrylates, polyalkyl (meth)acrylates, or fluorinated polyolefines, such as fluorinated ethylene or propylene, for example tetrafluoroethylene, preferably in combination with specific dioxols, such as perfluoro-2,2-dimethyl-1,3-dioxol. Mixtures of two or more of the above-mentioned materials are also possible.

Within the present invention silicon hydrogels, perfluoroalkyl polyethers or mixtures thereof, in particular silicon hydrogels, are the preferred hydrophobic organic bulk materials.

Examples of suitable silicon hydrogels are, for example, those currently used for the manufacture of extended wear contact lenses, for example copolymers of (i) one or more hydrophilic monomers, for example selected from the group of hydroxyethylacrylate, hydroxyethylmethacrylate, acrylamide, N,N-dimethyl acrylamide, a vinyl lactame such as N-vinylpyrrolidone, a (meth)acryloyloxyethyl phosphorylcholine, such as 2-acryloyloxyethyl phosphorylcholine or 2-methacryloyloxyethyl-2'-(trimethylammonium)ethyl phosphoryl-choline, N-vinyloxycarbonyl-L-alanine, acrylic or methacrylic acid; and (ii) a monomer and/or macromonomer comprising a siloxane bond or silane group, e.g. trimethylsilyl group. Examples of the latter group are tris-trimethylsilyloxy-silyl-propyl methacrylate (TRIS) or tris-trimethylsilyloxy-silyl-propyl vinyl carbamate (TRIS-VC), a polydimethylsiloxane having a carbon-carbon double bond at one single terminal, or a polydimethylsiloxane crosslinker having either a carbon-carbon double bond at both terminals or two or more pendent C—C double bonds, for example, as described in formula (2) below. Examples of suitable commercially available silicon hydrogels are Balafilcon A, Galyfilcon A, Lotrafilcon A, Lotrafilcon B or Senofilcon A.

Another group of preferred silicon hydrogels are amphiphilic segmented copolymers comprising at least one hydrophobic silicon or perfluoroalkyl polyether segment and at least one hydrophilic segment which are linked through a bond or a bridge member. Examples of said silicon hydrogels are disclosed, for example, in PCT applications WO 96/31792 and WO 97/49740 which are herewith incorporated by reference. A particularly preferred amphiphilic segmented copolymer comprises at least one hydrophobic segment selected from the group consisting of a polysiloxane, perfluoroalkyl polyether and a mixed polysiloxane/perfluoroalkyl polyether segment, and at least one hydrophilic segment selected from the group consisting of a polyoxazoline, poly(2-hydroxyethylacrylate), poly(2-hydroxyethylmethacrylate), polyacrylamide, poly(N,N-dimethylacrylamide), polyvinylpyrrolidone and a polyethyleneoxide segment.

Still another group of preferred silicon hydrogels are those obtainable by crosslinking a crosslinkable or polymerizable prepolymer that is obtainable by (a) copolymerizing at least one hydrophilic monomer having one ethylenically unsaturated double bond and at least one silicon crosslinker comprising two or more ethylenically unsaturated double bonds in the presence of a chain transfer agent having a functional group; and (b) reacting one or more functional groups of the resulting copolymer with an organic compound having an ethylenically unsaturated group. Silicon hydrogels of this type are disclosed, for example in WO 01/71392 which is herewith incorporated by reference.

A particularly preferred silicon hydrogel is obtained by crosslinking a prepolymer which is obtainable by (a) copolymerizing a hydrophilic monomer of the formula

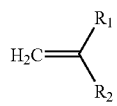

(1)

wherein $R_1$ is hydrogen or methyl, and $R_2$ is —COO—$(CH_2)_2$—OH, —$CONH_2$, —$CON(CH_3)_2$,

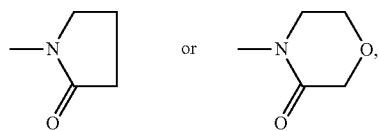

optionally in admixture with one or more further hydrophilic monomers; and a polysiloxane crosslinker that corresponds to formula

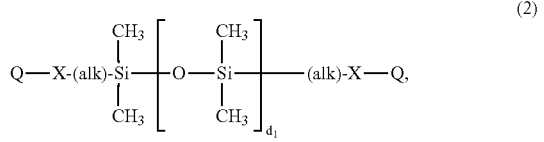

(2)

wherein $d_1$ is an integer from 10 to 500, preferably 10 to 300, more preferably 20 to 200 and in particular 25 to 150, (alk) is linear or branched $C_2$-$C_4$ alkylene or a radical —$(CH_2)_{1-3}$—O—$(CH_2)_{1-3}$-, X is —O— or —NH— and Q is a radical of the formula

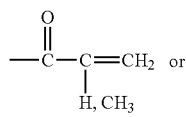

-continued $$-\overset{O}{\underset{}{C}}-NH-(CH_2)_{2-4}-O-\overset{O}{\underset{}{C}}-\underset{H,CH_3}{\overset{|}{C}}=CH_2;$$

in the presence of a chain transfer agent having a functional group, in particular 2-mercapto-ethanol or especially 2-aminoethane thiol (cysteamine); and (b) reacting the resulting copolymer with an organic compound having an ethylenically unsaturated group, for example with 2-isocyanatoethylmethacrylate (IEM), 2-vinyl-azlactone, 2-vinyl-4,4-dimethyl-azlactone, acryloyl or methacryloyl chloride, 2-hydroxyethylacrylate (HEA), 2-hydroxymethacrylate (HEMA), glycidylacrylate or glycidylmethacrylat, in particular with IEM or acryloyl chloride.

The polyanionic compound employed in the process of the invention is preferably a carboxyl functional polymer, that is a polymer having carboxyl groups. Examples of suitable carboxyl functional polymers are a polyacrylic acid; a polymethacrylic acid; a polyitaconic acid; a copolymer of two or more different carboxyl functional monomers, for example selected from the group consisting of acrylic acid, methacrylic acid, maleic acid, maleic anhydride and itaconic acid; or a copolymer of one or more carboxylic acids, for example, of the group acrylic acid, methacrylic acid, maleic acid, maleic anhydride and itaconic acid and one or more suitable non-ionic vinyl monomers, for example, of the group N-vinylpyrrolidone, methylvinylether, acrylamide, N,N-dimethylacrylamide, vinyl acetate, HEA. HEMA and a monovinyl polyethylene oxide; the above term copolymer is also meant to cover suitable block copolymers.

Preferably, the polyanionic compound is a polyacrylic acid or a copolymer of acrylic acid and one of the above mentioned further carboxyl functional monomers or non-ionic monomers, in particular a polyacrylic acid.

The number average molecular weight $M_n$ of the polyanionic compound is >5000, preferably ≧15000 and more preferably ≧20000. The upper limit of $M_n$ is in general not critical, anionic polymers being suitable up to a number average molecular weight of 1 million or above. Accordingly, a number average molecular weight $M_n$ of the polyanionic compound of from 7500 to 1.3 million, preferably from 7500 to 1 million, more preferably from 20000 to 1 million, even more preferably from 20000 to 750000, and in particular from 80000 to 500000, has proven as valuable.

A suitable organic solvent for the polyanionic compound is in principle every solvent with the ability to swell the organic bulk material underlying the biomedical article. Preferred solvents are, for example, alcohols, for example a $C_2$-$C_4$-alcohol, in particular ethanol or n- or isopropanol, especially ethanol; glycol ethers, for example a diethyleneglycol mono-$C_1$-$C_4$-alkylether, in particular diethyleneglycol monomethyl ether, diethyleneglycol monoethyl ether (DEGME), diethyleneglycol diethyl ether or diethyleneglycol monobutyl ether.

The preferred organic solvent is ethanol. It is also possible to use a mixture of two or more of the above-mentioned organic solvents. The presence of water severely affects the efficiency of the process and therefore should be limited as much as possible. Accordingly, it is preferred to employ a solution into the process comprising less than 20%, preferably less than 10%, more preferably less than 5%, and in particular less than 2% of water.

The solution of the polyanionic compound for treatment of the biomedical article in general has an acidic pH value; the preferred pH value is ≦5, more preferably ≦4, even more preferably from 1.5 to 3.5, and in particular from 1.8 to 3.

The solution for treatment of the biomedical article is devoid of a cationic polymer.

In general, rather diluted solutions of the polyanionic compound are employed in the process of the invention. Accordingly, the concentration of the polyanionic compound in the organic solvent is, for example from 0.1 to 25 g/l, preferably from 1 to 15 g/l, and most preferably from 3 to 10 g/l of solvent.

A preferred treatment solution according to the present invention is a solution of a polyacrylic acid or a copolymer of acrylic acid and a comonomer selected from the group consisting of methacrylic acid, maleic acid, maleic anhydride, itaconic acid, N-vinylpyrrolidone, methylvinylether, acrylamide, N,N-dimethylacrylamide and a monovinyl polyethylene oxide, in a $C_2$-$C_4$-alcohol or diethyleneglycol mono-$C_1$-$C_4$-alkylether, wherein the number average molecular weight $M_n$ of the polyacrylic acid homo- or copolymer is from 7500 to 1 million, and wherein the pH value of the solution is ≦4.

A more preferred treatment solution according to the present invention is a solution of a polyacrylic acid having a number average molecular weight $M_n$ of from 20000 to 750000 in ethanol, wherein the pH value of the solution is from 1.5 to 3.5 and in particular from 1.8 to 3.

The treatment solutions of the present invention may be prepared in a manner known per se, for example by simple mixing of the ingredients, which are likewise known per se and in general commercially available. The pH adjustment towards more acidic pH values may be performed, for example, by the addition of gaseous HCl. Certain solutions of anhydrous acids in organic solvents, such as ethanol/HCl, are also commercially available.

The treatment of the biomedical article with the treatment solution is suitably performed under ambient conditions or at an elevated temperature depending on the solvent used. For example, a temperature of from 10 to 50° C., preferably from 15 to 45° C. is employed. In case of water as the solvent, room temperature, that is a temperature of, for example, from 10 to 35° C. and preferably from 15 to 25° C. is preferably used for the treatment.

The treatment may be accomplished according to processes known per se. For example, the biomedical article is immersed in the treatment solution, or the treatment solution is deposited on the biomedical article surface, for example, by dipping, spraying, printing, spreading, pouring, rolling or spin coating, spraying or particularly dipping being preferred.

The treatment takes place for a time period of ≦5 minutes, preferably ≦1 minute, more preferably ≦30 seconds and in particular ≦10 seconds. Following the treatment with the polyanionic compound, the biomedical article is removed from the treatment solution and worked up, for example, as described below.

According to a preferred embodiment of the invention, the biomedical article—following its removal from the treatment solution—is contacted with a solvent, which has the ability to shrink the organic bulk material underlying the biomedical article, but which is miscible with the solvent of the treatment solution. Suitable solvents for this follow-up step are, for example, water, ethylene glycol, glycerol, 1,3-propanediol, or mixtures thereof. A preferred solvent for the follow-up step is water. Preferably, the biomedical article—following its removal from the treatment solution is dipped/immersed directly into the solution. The time period for the follow-up step is not critical; usually a time period of ≦1 minute, preferably ≦30 seconds more preferably ≦10 seconds is sufficient to accomplish the shrinkage of the bulk material.

It is further preferred that following the shrinkage step the biomedical article is treated with an aqueous solution comprising a neutral or slightly basic pH, for example a pH value of 7 to 10, preferably from 7.5 to 10, and in particular from 7.5 to 9.5. The aqueous solution advantageously may contain further ingredients, for example a salt, in particular sodium chloride, or a suitable buffer, for example a phosphate buffer. The preferred treatment is again dipping/immersing the biomedical article into the aqueous solution. The time period for this additional neutralization step is again not critical; usually a time period of ≦1 minute, preferably ≦30 seconds more preferably ≦10 seconds is sufficient to accomplish a further improvement of the surface coating. It is also possible to combine the shrinkage step and this further neutralization step. For example, shrinkage and neutralization may be done in one step by dipping the biomedical article in an aqueous solution of a weak base having a pH of, for example, from 7.5 to 10, for example in an aqueous $NaHCO_3$ or the like solution.

The biomedical article then may be worked up and finished in a usual manner. For example, contact lenses are in general subjected to a sterilization step, which comprises, for example, autoclaving the contact lenses for a certain time period at an elevated temperature. For example, autoclaving for a time period of 20 minutes to 1.5 hours, in particular from 30 minutes to 1 hour, at a temperature of about 115 to 130° C., has proven as valuable.

According to the process of the invention, biomedical articles, in particular ophthalmic articles, are obtained that have a variety of unexpected advantages over those of the prior art, which make those articles very suitable for practical purposes, e.g. as contact lens for extended wear. For example, they do have a high surface wettability and lubricity. This can be demonstrated, for example, by the finger tip test showing a very slippery article surface; or by visual inspection; or by suitable contact angle measurements. For example, sessile drop static contact angles of coated and non-coated lenses are determined with a DSA 10 drop shape analysis system from Krüss (Krüss GmbH, Hamburg, Germany). While uncoated silicon hydrogel contact lenses in general have a water contact angle of 90 to 100° or above, a treatment according to the process of the invention significantly reduces said value. Further tools for assessing the superior quality of the surface coatings obtainable according to the process of the invention are ATR-FTIR measurements or the Sudan Black dye absorption test as described below in the Examples section.

In addition, biomedical devices, e.g. ophthalmic devices such as contact lenses, comprising a composite material of the invention have a very pronounced biocompatibility combined with good mechanical properties. Generally, there is low microbial adhesion and low bio-erosion while good mechanical properties can be for example found in a low friction coefficient and low abrasion properties. Moreover, the dimensional stability of the composite materials of the invention is excellent. In addition, the attachment of a hydrophilic surface coating at a given bulk material according to the invention does not affect its visual transparency.

According to the process of the invention biomedical articles such as contact lenses may be coated very fast, that is within seconds; nevertheless the coated articles are mechanically very stable and robust. No pre-treatment step or the like is necessary, the lenses may be coated directly following their manufacture. This makes the process of the invention highly adaptable into a high volume mass production process, such as the contact lens manufacturing process as disclosed in EP-A-969956 or EP-A-1047542.

It is particularly surprising that the surface treatment according to the present invention in general does not affect the properties of the underlying organic bulk material. While prior art coating processes often affect article properties such as transparency, ion permeability, oxygen transmissibility, water contents or device geometry (e.g. diameter of a contact lens), said parameters are not or at least not significantly affected by the process of the invention.

In the examples, if not indicated otherwise, amounts are amounts by weight; temperatures are given in degrees Celsius. Average water contact angles of coated and non-coated lenses are determined as described above.

EXAMPLES

Example 1

Preparation of a Treatment Solution 0.36 g of solid polyacrylic acid ($M_n$=90.000, Polyscience) is dissolved in a mixture of 80 ml ethanol (Merck # 1.00983.2511) and 0.98 ml of a 1.5 M hydrochloric acid in ethanol (Fluka # 19934) and diluted by additional EtOH to 100 ml total volume.

A droplet of the treatment solution indicates pH=2.0 with wet pH indicator paper (Merck # 1.09540.000).

Example 2

Preparation of a Soft Silicon Hydrogel Contact Lens Having Attached to its Surface a Polyacrylic Acid Coating (i) Preparation of the Silicon Hydrogel Contact Lens
(ia) Preparation of PDMS Crosslinker I In a 4-L beaker, 24.13 g of $Na_2CO_3$, 80 g of NaCl and 1.52 kg of deionized water are mixed to dissolve. In a separate 4-L beaker, 700 g of bis-3-aminopropyl-polydimethylsiloxane (Shin-Etsu, MW ca. 11500) are dissolved in 1000 g of hexane. A 4-L reactor is equipped with overhead stirring with turbine agitator and a 250-mL addition funnel with micro-flow controller. The two solutions are then charged to the reactor, and mixed for 15 minutes with heavy agitation to produce an emulsion. 14.5 g of acryloyl chloride are dissolved in 100 mL of hexane and charged to the addition funnel. The acryloyl chloride solution is added dropwise to the emulsion under heavy agitation over one hour. The emulsion is stirred for 30 minutes on completion of the addition and then agitation is stopped and the phases are allowed to separate overnight. The aqueous phase is decanted and the organic phase is washed twice with a mixture of 2.0 kg of 2.5% NaCl dissolved in water. The organic phase is then dried over magnesium sulfate, filtered to 1.0 µm exclusion, and concentrated on a rotary evaporator. The resulting oil is further purified by high-vacuum drying to constant weight. Analysis of the resulting product by titration reveals 0.175 mEq/g of C=C double bonds.

(ib) Preparation of PDMS Crosslinker II

In a 4-L beaker, 61.73 g of $Na_2CO_3$, 80 g of NaCl and 1.52 kg of deionized water are mixed to dissolve. In a separate 4-L beaker, 700 g of bis-3-aminopropyl-polydimethylsiloaxane (Shin-Etsu, MW ca. 4500) are dissolved in 1000 g of hexane. A 4-L reactor is equipped with overhead stirring with turbine agitator and a 250-mL addition funnel with micro-flow controller. The two solutions are then charged to the reactor, and mixed for 15 minutes with heavy agitation to produce an emulsion. 36.6 g of acryloyl chloride is dissolved in 100 mL of hexane and charged to the addition funnel. The acryloyl chloride solution is added dropwise to the emulsion under heavy agitation over one hour. The emulsion is stirred for 30 minutes on completion of the addition and then agitation is stopped and the phases are allowed to separate overnight. The aqueous phase is decanted and the organic phase is washed twice with a mixture of 2.0 kg of 2.5% NaCl dissolved in water. The organic phase is then dried over magnesium sulfate, filtered to 1.0 µm exclusion, and concentrated on a rotary evaporator. The resulting oil is further purified by high-vacuum drying to constant weight. Analysis of the resulting product by titration reveals 0.435 mEq/g of C=C double bonds.

(ic) Preparation of the Crosslinkable Copolymer

A 2-L jacketed reactor is equipped with a heating/chilling loop, reflux condenser, $N_2$-inlet/vacuum adapter, feeding tube adapter and overhead mechanical stirring. A solution is generated by dissolving 90.00 g of PDMS crosslinker I according to (ia) and 30.00 g of PDMS crosslinker II according to (ib) in 480 g of 1-propanol. This solution is charged to the reactor and cooled to 8° C. The solution is degassed by evacuating to less than 15 mBar, holding at vacuum for 15 minutes, and then re-pressurizing with dry nitrogen. This degas procedure is repeated for a total of 3 times. The reactor is held under a blanket of dry nitrogen.

In a separate flask, a monomer solution is prepared by mixing 1.50 g of cysteamine hydrochloride, 0.3 g of AIBN, 55.275 g of DMA, 18.43 g of HEA and 364.5 g of 1-propanol. This solution is filtered with a Waterman 540 filter paper, and then added to the reactor through a degas unit and HPLC pump with a flow rate of 3.0 mL/minute. The reaction temperature is then elevated to 68° C. with a heating ramp about one hour.

In a second flask, a feeding solution is prepared by mixing 4.5 g of cysteamine hydrochloride and 395.5 g of 1-propanol and then filtering with Waterman 540 filter paper. When the reactor temperature reaches 68° C., this solution is slowly dosed into the reactor through the degasser/HPLC pump over 3 hours. The reaction is then continued at 68° C. for an additional 3 hours, on which heating has discontinued and the reactor is allowed to cool to room temperature.

The reaction mixture is transferred to a flask and stripped solvent at 40° C. under vacuum on a rotary evaporator until 1000 g of sample remained. The solution is then slowly mixed with 2000 g of deionized water with rapid agitation. Additional solvent is further removed until about 2000 g of sample remain. During this stripping process, the solution gradually becomes an emulsion. The resulting material is purified by ultrafiltration over a 10 kD molecular weight cut-off membrane until the permeate conductance is below 2.5 µS/cm.

This emulsion is then charged to a 2-L reactor equipped with overhead stirring, refrigeration loop, thermometer, and the pH meter and dispensing tip of a Metrohm Model 718 STAT Titrino. The reaction mixture is then cooled to 1° C. 7.99 g of $NaHCO_3$ are charged to the emulsion and stirred to dissolve. The Titrino is set to maintain pH at 9.5 by intermittent addition of 15% sodium hydroxide solution. 11.59 mL of acryloyl chloride are then added over one hour using a syringe pump. The emulsion is stirred for another hour, then the Titrino is set to neutralize the reaction mixture by addition of a 15% solution of hydrochloric acid. The product is purified by ultrafiltration again with 10 kD molecular weight cut-off membrane until the permeate conductance is below 2.5 µS/cm. The final macromonomer is isolated by lypophilization.

(id) Preparation of Contact Lenses 18.83 g of the polymer obtained according to step (ic) are dissolved in approximately 200 mL of 1-propanol, concentrated to ca. 70 g total solution weight, and filtered to 0.45 µm exclusion. 67.94 g of solution at 26.53% solids are recovered. 4.503 g of a 1% solution of 2-hydroxy-4'-hydroxyethyl-2-methylpropiophenone (IRGACURE®-2959, Ciba Specialty Chemicals) are added, and the solution is then concentrated to a final formulation having 60% solids.

200 mg of the formulation are dosed into poly(propylene) contact lens molds and the molds are closed. The molds are then irradiated for 15 s with an ultraviolet light source having an intensity of 2.18 mW/cm². The molds are then opened, and the contact lenses are removed from the mold halves.

(ie) Preparation of the Surface Coating

A hydrophobic silicon hydrogel contact lens obtained according to (id) above is placed on a lens holder. The lens holder with the lens is then immersed at room temperature for 5 sec into the treatment solution obtained according to Example 1. Following its removal from the treatment solution, the lens holder with the lens is rinsed for 2 sec in a water bath and subsequently treated for 2 sec in a phosphate buffered saline (pH 7.2). The contact lens is then transferred into a glass vial and sterilized for 30 min at 121° C. by autoclaving. The presence of the polyacrylic acid coating is proven by ATR-FTIR spectroscopy (absorption at 1720 cm$^{-1}$ at pH 2 and at 1560-1620 cm$^{-1}$ at pH 7.2). The hydrophilic surface coating is further investigated by visual wettability and hydrophilicity testing as well as contact angle measurements and the Sudan Black staining test (see Table I below).

Example 3

Preparation of a Soft Silicon Hydrogel Contact Lens having Attached to its Surface a Polyacrylic Acid Coating Hydrophobic silicon hydrogel contact lenses (lotrafilcon A, copolymerization product of a mixed polysiloxane/perfluoroalkyl polyether crosslinker, TRIS and DMA) are subjected to the surface treatment as described in Example 2 (ie). The results are summarized in Table I below.

Example 4

Preparation of a Soft Silicon Hydrogel Contact Lens having Attached to its Surface a Polyacrylic Acid Coating Hydrophobic silicon hydrogel contact lenses (lotrafilcon B, copolymerization product of a mixed polysiloxane/perfluoroalkyl polyether crosslinker, TRIS and DMA) are subjected to the surface treatment as described in Example 2 (ie). The results are summarized in Table I below.

Example 5

Preparation of a Soft Silicon Hydrogel Contact Lens having Attached to its Surface a Polyacrylic Acid Coating Hydrophobic silicon hydrogel contact lenses (galyfilcon, commercially available under the brand name Acuvue Advance®) are first of all extracted with 2-propanol (2 ml/lens), then rinsed with water several times and stored in a vessel in cold water.

For coating purposes a contact lens is taken directly out of the vessel and is subjected to the surface treatment as described in Example 2 (ie). The results are summarized in Table I below.

Example 6:

Surface Characterization (i) Wettability

Qualitative assessment by visual inspection of the contact lens. The ranking is based on the observation, how fast a film of the storage solution on the surface of the autoclaved contact lens vanishes following the removal of the lens from the storage vial with tweezers.

0=no wetting, i.e. no film on the surface, droplets at most
1=slight or partial wetting; a film is present but tears more or less immediately (<5 sec)
2=good wetting; a film on the surface is present and is rather stable ( film tearing >5 s)

(ii) Lubricity

Qualitative evaluation by contacting the lens surface with the finger tips.

0=tacky or frictional surface
1=indifferent surface with respect to tackiness/lubricity
2=slippery surface (iii) water contact angle The measurement is performed by the sessile drop method with a DSA 10 drop shape analysis system from Krüss GmbH, Germany with pure water (Fluka, surface tension 72.5 mN/M at 20° C.). For measurement purposes a contact lens is taken off the storage solution with tweezers and excess storage solution is removed by gentle shaking. The contact lens is placed on the male part of a contact lens mold and gently blotted with a dry and clean cloth. A water droplet (about 1 µl) is then dosed on the lens apex, and the change of the contact angle over time of this water droplet (WCA(t), circle fitting mode) is monitored; WCA is calculated by extrapolation of the graph WCA(t) to t=0.

(iv) ATR-FTIR

ATR-FTIR measurements are performed with a Nicolet FTIR spectrometer equipped with a ZnSe crystal in an overhead sample holder (45° angle of incidence) with micrometer controlled clamp-down facility. For measurement purposes, a dried contact lens (vacuum drying oven, 1 mbar, 25° C., 30 min) is placed on the crystal, fixed by the clamp and measured (about 256 scans). The ATR-Infrared absorbance spectra are all normalized to the signal at 2961 cm$^{-1}$; assessment by comparison of the signal increase at 1720 cm$^{-1}$ ($v_{COOH}$) with the signal at about 1631 cm$^{-1}$ ( indicative for silicon hydrogel presence).

n=no change
w=weak signal increase (<0.5)
m=moderate signal increase (0.5-1.0)
s=strong signal increase (>1)

(v) Sudan Black Dye Absorption Test

A 0.5% (w/w) Sudan Black dye solution is prepared by dissolving 0.5 g of Sudan Black B (Aldrich) over night in 100 g of vitamin E oil under stirring. For measurement purposes, the surface-treated lens is first of all autoclaved (30 min, 121° C.) in 2 ml of an phosphate buffered saline (pH 7.2) in a glass vial. The contact lens is then removed from the solution with tweezers and gently shaken so that most of the surface water is removed. The lens is then placed in the above prepared Sudan Black dye solution for 5 min. Thereafter the lens is removed from the dye-bath, and the excess dye solution is rinsed off with warm water. The lens is air-dried and assessed according to its degree of staining.

2=no or almost no staining
1=slight staining
0=considerable staining

The values obtained with contact lenses as coated in Examples 2-5 and with the corresponding uncoated contact lenses (control) are summarized in Table I.

TABLE I

| Example | Treatment time [sec] | Wetta-bility | Lubric-ity | WCA [°] | Sudan Black (wet) | ATR-FTIR |
|---|---|---|---|---|---|---|
| 2 | 5 | 2 | 2 | 16 | 2 | m |
| 2(Control) | — | 0 | 0 | 109 | 0 | n |
| 3 | 5 | 2 | 2 | 23 | 2 | s |
| 3(Control) | — | 0 | 0 | 105 | 0 | n |
| 4 | 5 | 2 | 2 | 18 | 2 | m |
| 4(Control) | — | 0 | 0 | 104 | 0 | n |
| 5 | 5 | 2 | 2 | 25 | 2 | Not measured |
| 5(Control) | — | 1 | 0 | 102 | 0 | Not measured |

Example 7

Preparation of a Polyacrylic Acid Coating on a Soft Silicone Hydrogel Contact Lens. Impact of Water Content and Treatment Time on the Hydrophilization of Lotrafilcon B Lenses (i) Preparation of Treatment Solutions (ia) An ethanolic lens treatment solution ("solution I") is prepared by dissolving 3.6 g of solid polyacrylic acid ($M_n$=90.000, Polyscience) in a mixture of 800 ml ethanol (Merck # 1.00983.2511) and 9.8 ml of a 1.5 M hydrochloric acid in ethanol (Fluka # 19934) and diluted by additional EtOH to 1000 ml total volume.

(ib) An aqueous lens treatment solution ("solution II") is prepared by dissolving 3.6 g of solid polyacrylic acid ($M_n$=90.000) in a solution of 700 ml water and 3.6 ml of a 1 N aqueous hydrochloric acid solution and diluted with additional water to 1000 ml total volume.

A droplet of each treatment solutions indicates pH=2.0 with wet pH indicator paper (Merck # 1.09540.000).

By mixing of appropriate volume portions of solution II ($V_{II}$) with those of solution I ($V_I$) lens treatment solutions with different water contents are prepared according to the following equation:

$$c_{H2O}=[V_{II}/(V_I+V_{II})]*100[\%]$$

(ii) Lens Coating Process: The lens coating processes are performed with Lotrafilcon B lenses as described in Example 2 (ie) by variation of the treatment time (5 s, 10s, 30 s, 60 s and 300 s) and water content of the treatment solution cH20 (0%, 5%, 20%, 50% and 100%).

(iii) Lens Surface Characterizations:

Lenses were evaluated and characterized by water contact angle, slipperiness, and Sudan Black staining test according to the methods described in Example 6.

The results are summarized in Tables 2 to 4 below.

TABLE 2

Impact of treatment time and water content of the treatment solution on water contact angle of Lotrafilcon B lenses

| | Treatment Time [s] | | | | |
|---|---|---|---|---|---|
| $c_{H2O}$ [%] | 5 | 10 | 30 | 60 | 300 |
| 0 | 19 | 21 | 20 | 25 | 14 |
| 5 | 17 | 37 | 31 | 24 | 21 |
| 20 | 46 | 43 | 42 | 36 | 36 |
| 50 | 66 | 71 | 49 | 52 | 57 |
| 100 | 84 | 90 | 83 | 90 | 79 |

TABLE 3

Impact of treatment time and water content of the treatment solution on lubricity of Lotrafilcon B lenses

| | Treatment Time [s] | | | | |
|---|---|---|---|---|---|
| $c_{H2O}$ [%] | 5 | 10 | 30 | 60 | 300 |
| 0 | 2 | 2 | 2 | 2 | 2 |
| 5 | 2 | 2 | 2 | 2 | 2 |
| 20 | 1 | 2 | 2 | 2 | 2 |
| 50 | 1 | 1 | 1 | 2 | 2 |
| 100 | 1 | 1 | 1 | 1 | 1 |

TABLE 4

Impact of treatment time and water content of the treatment solution on the Sudan Black dye absorption test of Lotrafilcon B lenses

| | Treatment Time [s] | | | | |
|---|---|---|---|---|---|
| $c_{H2O}$ [%] | 5 | 10 | 30 | 60 | 300 |
| 0 | 2 | 2 | 2 | 2 | 2 |
| 5 | 2 | 1 | 2 | 2 | 2 |
| 20 | 1 | 1 | 1 | 2 | 2 |
| 50 | 0 | 0 | 1 | 1 | 1 |
| 100 | 0 | 0 | 0 | 0 | 0 |

The invention claimed is:

1. A process for the hydrophilic coating of a soft contact lens comprising a hydrophobic bulk material selected from the group consisting of a silicon hydrogel, a perfluoroalkyl polyether and a mixture thereof, comprising: treating the soft contact lens for a time period of ≦5 minutes with a solution of an organic solvent comprising a polyanionic compound with a number average molecular weight $M_n$ of >5000, wherein the solution comprises less than 20% by weight of water, and wherein the solution is devoid of a cationic polymer.

2. A process according to claim 1, wherein the solution comprises less than 10% by weight of water.

3. A process according to claim 1, wherein the polyanionic compound is a polyacrylic acid or a copolymer of acrylic acid and a comonomer selected from the group consisting of methacrylic acid, itaconic acid, maleic acid, maleic anhydride, N-vinylpyrrolidone, methylvinylether, acrylamide, N,N-dimethylacrylamide and a monovinyl polyethylene oxide, in particular a polyacrylic acid.

4. A process according to claim 1, wherein the number average molecular weight $M_n$ of the polyanionic compound is from 7500 to 1 million, preferably from 20000 to 750000, and in particular from 80000 to 500000.

5. A process according to claim 1, wherein the organic solvent is a $C_2$-$C_4$-alcohol or a glycol ether, in particular ethanol or diethylene glycol monoethylether.

6. A process according to claim 1, wherein the solution for treatment of the soft contact lens is a solution of a polyacrylic acid or a copolymer of acrylic acid and a comonomer selected from the group consisting of methacrylic acid, maleic acid, maleic anhydride, itaconic acid, N-vinylpyrrolidone, methylvinylether, acrylamide, N,N-dimethylacrylamide and a monovinyl polyethylene oxide, in a $C_2$-$C_4$-alcohol or a diethyleneglycol mono-$C_1$-$C_4$-alkylether, wherein the number average molecular weight $M_n$ of the polyacrylic acid homo- or copolymer is from 7500 to 1 million, and wherein the pH value of the solution is $\leq 4$.

7. A process according to claim 1, wherein the solution for treatment of the soft contact lens is a solution of a polyacrylic acid having a number average molecular weight $M_n$ of from 20000 to 500000 in ethanol, wherein the pH value of the solution is from 1.5 to 3.5 and in particular from 1.8 to 3.

8. A process according to claim 1, wherein the time period of the treatment is $\leq 1$ minute, preferably $\leq 30$ seconds and in particular $\leq 10$ seconds.

9. A process according to claim 1, further comprising a step of contacting the soft contact lens with a solvent after the biomedical article is removed from the treatment solution, wherein the solvent has the ability to shrink the organic bulk material underlying the biomedical article, and wherein the solvent is miscible with the solvent of the treatment solution.

10. A process according to claim 9, further comprising a step of treating the biomedical article, after the shrinking step, with an aqueous solution comprising a neutral or slightly basic pH.

11. The coated soft contact lens made according to claim 1.

* * * * *